(12) United States Patent
Kraus

(10) Patent No.: US 9,474,900 B2
(45) Date of Patent: Oct. 25, 2016

(54) POLARIZATION DEVICE AND IMPLANTATION DEVICE

(75) Inventors: Werner Kraus, Munich (DE); Peter Willsau, legal representative, Munich (DE)

(73) Assignee: Bjarne Geiges, Munich (DE)

( * ) Notice: Subject to any disclaimer, the term of this patent is extended or adjusted under 35 U.S.C. 154(b) by 1123 days.

(21) Appl. No.: 13/381,461

(22) PCT Filed: Jun. 30, 2010

(86) PCT No.: PCT/EP2010/003954
§ 371 (c)(1),
(2), (4) Date: Feb. 16, 2012

(87) PCT Pub. No.: WO2011/000556
PCT Pub. Date: Jan. 6, 2011

(65) Prior Publication Data
US 2012/0277812 A1    Nov. 1, 2012

(30) Foreign Application Priority Data
Jun. 30, 2009    (DE) .................. 10 2009 031 134

(51) Int. Cl.
*A61N 1/32*    (2006.01)
*A61B 17/86*    (2006.01)
*A61N 1/05*    (2006.01)

(52) U.S. Cl.
CPC ............... *A61N 1/326* (2013.01); *A61B 17/86* (2013.01); *A61N 1/05* (2013.01)

(58) Field of Classification Search
CPC ......... A61N 1/205; A61N 1/326; A61N 1/40

USPC ...................................................... 607/50–52
See application file for complete search history.

(56) References Cited

U.S. PATENT DOCUMENTS

| 3,918,440 A | 11/1975 | Kraus |
| 4,611,597 A | 9/1986 | Kraus |
| 5,292,252 A * | 3/1994 | Nickerson et al. ........... 433/173 |
| 6,778,861 B1 | 8/2004 | Liebrecht et al. |

FOREIGN PATENT DOCUMENTS

| DE | 2 311 817 A1 | 9/1974 |
| DE | 23 11 817 C2 | 6/1984 |
| DE | 39 42 735 A1 | 6/1991 |

(Continued)

OTHER PUBLICATIONS

International Search Report dated Dec. 27, 2010 including English-language translation (Ten (10) pages).

*Primary Examiner* — Eugene Wu
(74) *Attorney, Agent, or Firm* — Crowell & Moring LLP

(57) ABSTRACT

The invention relates to a device for polarizing at least two spatially separated, at least partially electrically conductive implants. The device includes a coil having a first pole and a second pole, a first contact device associated with the first pole for electrically contacting a first implant, and a second contact device associated with the second pole for electrically contacting a second implant. The coil may be arranged directly or indirectly on or in the first implant and carried by the first implant. The second contact device may include a flexible electrical line which allows the second implant to be contacted in a manner such that the coil may be arranged in a spatially separated manner from the second implant.

16 Claims, 6 Drawing Sheets

(56) References Cited

FOREIGN PATENT DOCUMENTS

| | | |
|---|---|---|
| DE | 42 30 181 A1 | 3/1994 |
| DE | 199 28 449 C1 | 3/2001 |
| EP | 0 108 383 A2 | 5/1984 |
| EP | 2074958 A2 * 7/2009 ............. A61B 17/86 |

* cited by examiner

POLARIZATION DEVICE AND IMPLANTATION DEVICE

BACKGROUND AND SUMMARY OF THE INVENTION

The invention relates to a device for polarizing implants as well as an implantation system comprising such a device.

Polarization devices and implantation systems are known in the field of osteosynthesis. Osteosynthesis serves the load-stable fixation of the fragments of a broken or ill bone in its uninjured, natural form by means of implanted screws, support plates, wires, bone marrow nails and the like which are usually made of non-corroding steel or titanium alloys. These osteosynthesis means enable a rapid mobilisation of the patients while, at the same time, the injured bone is steadied which is a vital requirement for its healing.

Problematic with the rigid fixation by means of the comparably inelastic, tissue-removing support implants, however, is the interference with the biological regeneration primarily due to the loss of blood vessels and nerves. In addition the biomechanical quality of the support structure will suffer due to the partial loss of its function with the implantation time increasing. Together with the loss of the biological control, however, the risk of an infection caused by resistant bacteria (MRSA=multi-resistant staphylococcus aureus) will increase. It was shown that these may colonise the surface of metal implants in the form of an adherent biofilm and withstand the attack of antibiotics by means of a glycocalyx of polysaccharides.

These problems can be addressed within the framework of orthopaedic surgery by electro-osteotherapy using, for example, the generic contact device mentioned in the introduction as, for example, described in U.S. Pat. No. 6,778,861 B1. In the magnetically induced electro-osteotherapy illustrated there alternating electric potentials having a low frequency are induced in osteosynthesis means by exposing an affected body part to an alternating magnetic field. For a long time it has been shown in numerous clinical applications of the technique according to the method to chronically therapy-resistant, in most cases infected bone defects, cysts and tumour metastases as well as in clinic-oriented experimental studies that an optimum healing effect is obtained in the bone region abutting on the support metal by using the osteosynthesis implants as sources of extremely low-frequency sinusoidal alternating electric potentials.

The transmission technology functions in accordance with the transformer principle: The injured or ill body region is flooded with an extremely low-frequency, sinusoidally extending magnetic field having a frequency of approximately 1 to 100 Hz—preferably of 4 to 20 Hz—and a magnetic flux density of 0.5 to 5 mT (5 to 50 Gauss) generated by a function generator in one or more primary external current coils into which the body part provided with the osteosynthesis means is introduced. These extremely low-frequency electromagnetic fields permeate the tissue including potential clothing and a cast as well as the non-magnetic (austenitic) support metals of the osteosynthesis largely without loss. A secondary coil assembly, the so-called transformer, is implanted in electric contact with these. The electrical potentials induced in the transformer are thus brought to bear in the area of the bone lesion as well as generally in the tissue adjacent to the osteosynthesis means.

With this technology of the inductive transmission of therapeutically effective electrical potentials to the components of the osteosynthesis the danger of infection is avoided by percutaneous current lines, and the treatment parameters electric voltage, frequency, intensity, signal form and treatment time can be specified by the indication specific programming of a function current generator of the induced magnetic field.

Another example of an implant which can be used within the framework of the electro-osteotherapy is specified in German Patent Publication No. DE 23 11 817 C 2 and U.S. Pat. No. 3,918,440. The snap fastener screw described here is contacted to a repeating coil disposed outside of the screw via a snap fastener and thus becomes a part of the electro-osteotherapy.

The invention is based on the object to provide a possibility of a multi-variant integration of implants into electro-osteotherapy, wherein in particular a compact arrangement which is readily lasting for the aspired implantation period is aimed at.

The invention includes a device for polarizing at least two spatially separated, electrically at least partially conductive implants comprising
  a coil having a first pole and a second pole,
  a first contact device allocated to the first pole for electrically contacting a first implant,
  at least one second contact device allocated to the second pole for electrically contacting at least one second implant,
  wherein the coil is arranged directly or indirectly on or in the first implant and can be carried by it, and
  wherein the at least one second contact device comprises a flexible electric line which enables the at least one second implant to be contacted so that the coil can be arranged so as to be spatially separated from the at least one second implant.

In contrast to the known state of the art the implants thus do not only service fixation purposes and serve as an electrode, but the first implant, at the same time, also serves as the carrier of the repeating coil. The counter electrode is formed by another, structurally identical or also entirely different implant by establishing a line connection from the coil carried by the first implant to the other implant, wherein, of course, also a plurality of implants can be contacted by such line connections so that each of these implants forms a counter electrode to the implant carrying the coil. All the involved implants may be structurally identical or formed differently.

It is particularly preferable that the coil can be arranged in a cavity of the first implant and that the first contact device electrically contacts the first implant within the cavity. In this way the coil is safely accommodated in the human body. In particular, the connection between the coil and the first implant is absolutely secure and interference immune since this connection is in no way influenced by any processes in the human body.

It is useful that the coil is wound on a magnetically conductive core. In this way the conversion of the energy applied by an external magnetic field into an electrical voltage will become more efficient.

The invention develops its advantages particularly in connection with the first and/or the at least one second implant being a bone screw. Bone screws can have a multitude of functions and are comparably readily implantable at various positions of the body. Insofar the present invention can be used in a particular flexible manner in connection with bone screws.

The invention is, here, usefully further developed in that the at least one second contact device comprises a contact snap fastener through which a mechanical and electrical connection to the at least one second implant can be established. Since it is a matter of a simple handling of the components to be implanted during the operation the connection of the second contact device to the second implant via a contact snap fastener is a particularly useful solution. A snap fastener is capable of simultaneously establishing a mechanical as well as an electrical connection.

It is particularly useful that at least one insulating sheath is provided by means of which the contact snap fastener of the at least one second contact device can be electrically insulated from the surrounding tissue. In this way the occurrence of bone growth in the area of the contact snap fastener is avoided which might be impedimental particularly with regard to the explantation of the implant or render additional intricate measures necessary.

For comparable reasons it may be contemplated that at least one insulating sheath is provided by means of which a proximal area of the bone screw can be electrically insulated from surrounding tissue.

For a good manageability of the components it is again usefully envisaged that the coil is retained by a bobbin through which a mechanical contact to the first implant can be established.

In this case as well it can advantageously be ensured that at least one insulating sheath is provided by means of which a proximal area of the bobbin can be electrically insulated from the surrounding tissue.

The bobbin can be handled in a particularly simple manner if it is ensured that the mechanical contact comprises a snap-on connection.

It is particularly advantageous that the bobbin accommodates a distributor to which a plurality of second contact devices is connected. The lines leading to the various second contact devices are therefore safely contacted within the bobbin.

The present invention may be further developed so that the coil is a component of an electric circuit comprising at least one further electrically effective component in addition to the coil. In this way additional functionalities can be provided.

It may, for example, be contemplated that, as the further electrically effective component, an accumulator is provided which is connected in parallel to the coil. In this way it is possible to sustain the electrical potentials of the implants even if currently no external magnetic field is present. The accumulator is charged by an external magnetic field during the treatment, a rectification of the induced alternating voltage being required for this purpose. In the absence of the external magnetic field the accumulator can then in turn deliver the stored energy by generating an electric voltage and a related current flow.

Usefully it may also be contemplated that a function generator is provided as a further electrically effective component. The signal shaping for generating the electric fields in the area of the implants thus does not have to be performed by the external magnetic field alone or at all. It is rather possible to provide a function generator which assumes this function. This is particularly useful in connection with an also provided accumulator which is charged by the coil in the presence of an external magnetic field. It may then also provide the voltage required for the operation of the function generator in the absence of an external magnetic field.

It may also be useful that, as the further electrically effective component, a circuit is provided which is capable of modifying an alternating voltage provided by the device so that the first implant has, at least predominantly, a first polarity while the second implant has, at least predominantly, a second polarity which is inverse to the first polarity. As is known the osteogenesis depends on the polarity of the respective electrode. The cathode encourages osteogenesis, and the anode hampers it. Consequently the right thing can be achieved by an appropriate rectification depending on the situation. The circuit can be realised discretely or as an integrated circuit, preferably as an ASIC.

According to a preferred embodiment of the invention it is contemplated that the further electrically effective component can be disposed in the cavity of the first implant. All electrically effective components are thus disposed at one location so that a snap fastener already described will be sufficient for contacting the second implants.

However, it is also possible that the further electrically effective component can be disposed in a cavity the second implant. This solution is to be preferred if there is not enough space available in the first implant to accommodate all components.

The invention further relates to an implantation system comprising at least two at least partially electrically conductive implants to be implanted so as to be spatially separated, and a device according to the invention.

Hence particularly an electromagnetically inducible pick-up coil above a magnetically conductive soft iron core is suggested which is inserted into the lumen of a hollow screw anchored in the vicinity of a bone defect. The pick-up coil is enveloped in an insulating layer of epoxy resin or silicone and connected to a coil spring or sheet metal spring with its lower end in an electrically conductive manner. With it contacts the bone screw upon insertion into the lumen of the screw. The upper end of the bobbin protrudes beyond the coil winding and is accommodated by a sheath of high-grade steel or titanium and mechanically retained by being adhered to it. At its upper end the sleeve has the shape of a snap fastener which is pushed into a seat in the head of the bone screw after the insertion of the pick-up coil. Within the sleeve, and insulated from it, the upper end of the winding of the pick-up coil leads to an electrical distribution to a plurality of, for example 1 to 3 or 4, cable connections having a length of, for example, 3 to 5 cm which, via electrical pressure contacts respectively provided in the head of further bone screws, polarizes the same relative to the screw carrying the pick-up coil. Other than in the device of the "bipolar induction screw system" (see below) in which both outputs of the pick-up coil are respectively contacted to the shaft and a tip insulated from it in the lumen of a hollow bone screw any hollow screws such as the ones used for the fixation and for steadying bone fragments can be used for the system of the mono- or unipolar induction screws according to the invention.

The hollow screws are preferably made of titanium alloys on the surface of which a poorly conducting oxide layer forms in the tissue. This can be prevented by a coating of highly conductive titanium niobium oxynitride (Ti, Nb)ON.

Another feature of the invention offers the possibility of a miniaturisation of the pick-up coil. By changing the gradient of the rising or falling slopes of the sine waves of the induced electromagnetic field at the same frequency the induced electric voltage can be increased at an unvaried amplitude, and thereby a loss caused by the miniaturisation of the pick-up coil can be compensated.

The Monopolar Induction Screw System (MISS) according to the invention differs from the Bipolar Induction Screw System (BISS) according to German Patent Publication No. DE 199 28 449 C1 particularly by the spatial distribution of the stimulating electric field in the bone. While the extension of the electric field only reaches the surface of the tissue layer directly contacting the screw in case of the bioplar induction screw the induced electric field extends between them across the entire volume of, for example, an extended fracture zone or a pathologically changed bone area which has to be filled with own and foreign bone or bone substitute and biologically integrated in case of the system of the monopolar induction screws according to the invention. The monopolar induction screw system ideally meets these requirements.

The device according to the invention is also clearly superior to the "snap fastener screw" according to German Patent Publication No. DE 23 11 817 C2 and U.S. Pat. No. 3,918,440. The drawback of this arrangement of the pick-up coils (the so-called transformers) having a diameter of 3 to 5 mm and a length of 50 mm implanted into the soft tissue becomes apparent in a limited service life of its relatively long cable connections of 5-10 cm to the osteosynthesis screws. Due to their limited fatigue resistance cable breaks frequently occurred within the required therapy time of 3 to 6 months if the pick-up coils grew into the soft tissue and followed the movements of muscles and tendons.

Materials for the insulating compound in the bobbin are, for example, polyetheretherketone (PEEK) and polyvinylidene fluoride (PVDF). Both materials are biocompatible, autoclavable and gamma ray sterilisable.

The cable connections preferably consist of fourfold coiled pacemaker wire MP35N comprising a cobalt base alloy.

The bone screws are preferably made of a titanium alloy having a conductance-enhancing coating of titanium niobium oxynitride (Ti, Nb)ON.

Experience has shown that, in case of the screws of the bipolar induction screw system (BISS), in the course of the therapeutically required therapy time of 3 to 5 months and daily induction times of 2 to 3 times 45 minutes new bone forms not only, as intended, around the shaft of the bipolar screw in the area of the bone defect, but also in the direct vicinity of the screw head. For the removal of the bipolar screws together with the other parts of a metal osteosynthesis (support plate, screws, wires, . . . ) which, from an orthopaedic point of view, should be regularly take place one year after the implantation, the very hard bone layer around the head of the bipolar screw constitutes a substantial complication. Hardness and thickness of this bone can only be removed using "heavy" tools, for example hammer and chisel. The risk of tissue metalloses due to, among other things, metal chips produced during this procedure can frequently not be avoided.

The undesired, potentially dangerous bone shell around the contact area (the snap fastener in the screw head) can be avoided by an insulating sheath around the pressure contact fastener the length of which also envelops the head of the contacted bone screw towards the bottom in such a way that any direct electrical contact to the bone is reliably avoided.

The sheath may, conveniently, be a part of the insulation of the distributor in the head of the snap fastener contact of PEEK or PVDF and close the snap fastener insert containing the pick-up coil and the cable distributor with its upper end having, for example, the form of a mushroom-shaped cap.

The cable connections between the distributor and the contact snap fasteners lead through the closing cap to the other monopolar bone screws of the system which are likewise encapsulated in an insulating fashion.

The invention will now be discussed by way of example with reference to the accompanying drawings making use of particularly preferred embodiments.

BRIEF DESCRIPTION OF THE DRAWINGS

In the following description of the drawings identical numerals designate identical or comparable components.

DETAILED DESCRIPTION OF THE DRAWINGS

Figure 1:
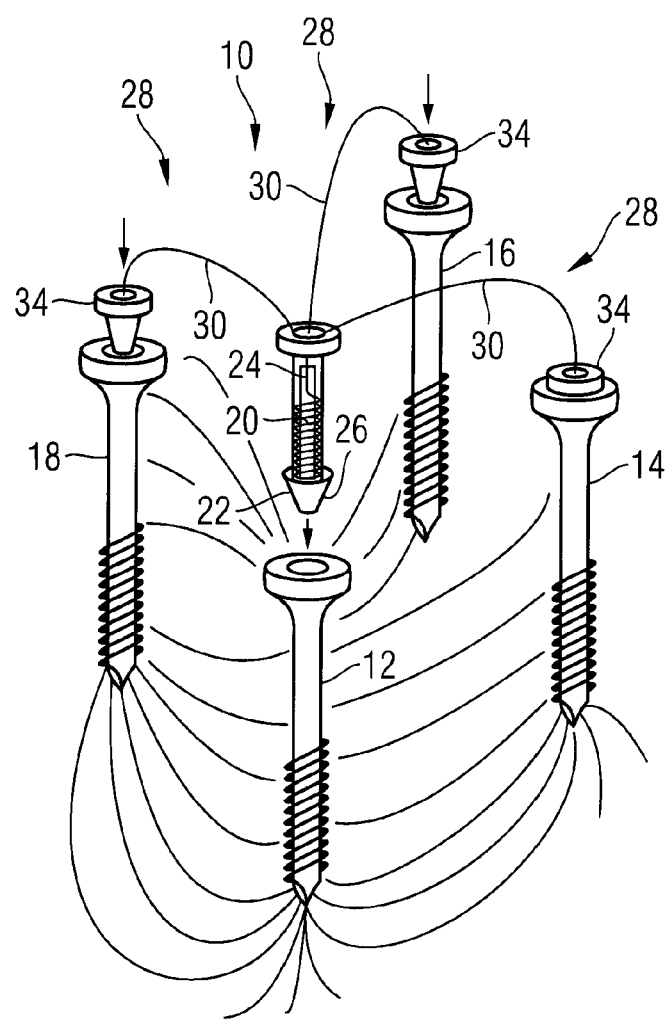
FIG. 1 shows a schematic perspective view of an implantation system according to the invention including associated bone screws.
Figure 2:
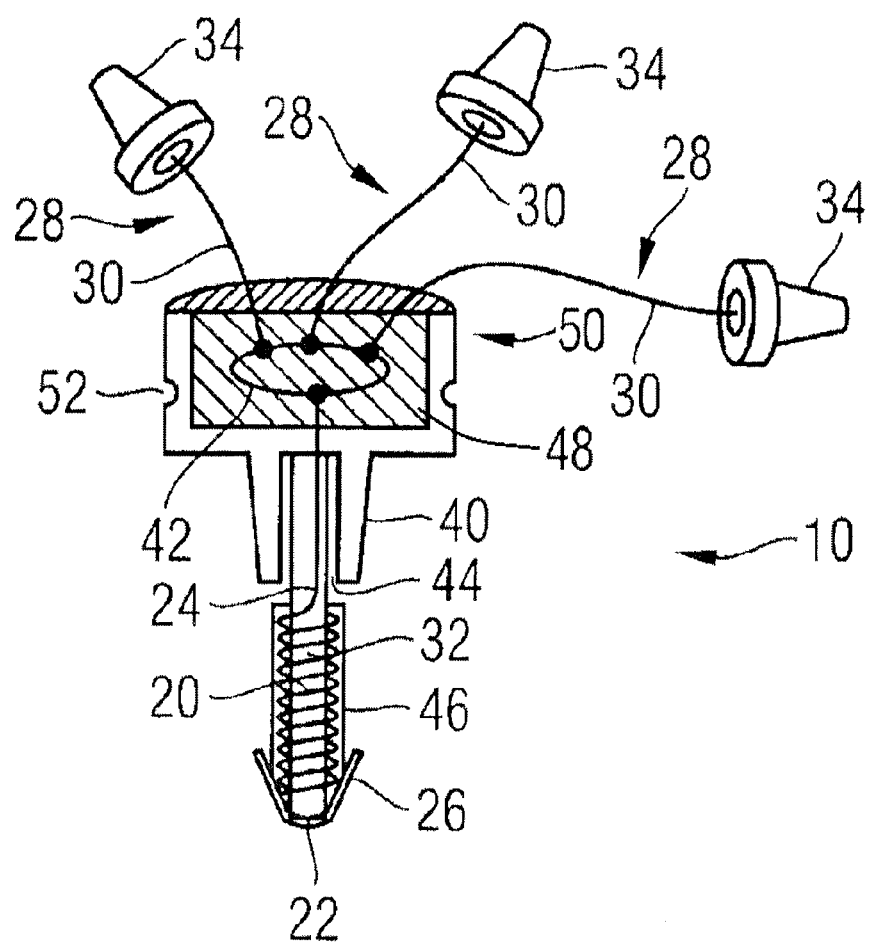
FIG. 2 shows a schematic perspective, partially cut view of a polarization device according to the invention.

FIG. 1 shows a schematic perspective view of an implantation system according to the invention including associated bone screws. FIG. 2 shows a schematic perspective, partially cut view of a polarization device according to the invention. Four bone screws 12, 14, 16, 18 as well as a polarization device 10 connected to or becoming connected to the bone screws 12, 14, 16, 18 are shown. The polarization device 10 contains a coil 20 wound on a magnetically conductive core 32. A first pole 22 of the coil 20 is connected to a contact device 26 which is formed as a contact spring. A second pole 24 of the coil 20 leads to a distributor 42. Three further contact devices 28 are connected to this distributor 42. These contact devices 28 comprise an electric line 30 and contact snap fasteners 34 on the ends of the lines 30 facing away from the distributor 42. In FIG. 1 the bone screw 14 is already connected to the associated contact snap fastener 34 while, with respect to the bone screws 16, 18, the associated contact snap fasteners 34 are shown immediately before they are connected to the bone screws 16, 18. The coil 20 is supported by a bobbin 40, for example indirectly in that the magnetically conductive core 32 onto which the coil 20 is wound is non-positively and/or positively accommodated in a recess 44 of the bobbin. The coil is enveloped by an insulating sheath 46 and thereby protected from electrically contacting the bone screw other than via the contact device 26 connected to the first pole 22. The distributor 42 is embedded in an insulating compound 48 consisting of, for example, PEEK or PVDF. The housing 50 comprising the recess 44 for retaining the coil 20 or the magnetically conductive core 32 has an at least in sections circumferential groove 52. The bone screw 12 to be connected to the first contact device 26 comprises a corresponding complementary device so that a stable snap-on connection between the housing 50 and the bone screw 12 can be provided.

Figure 3:
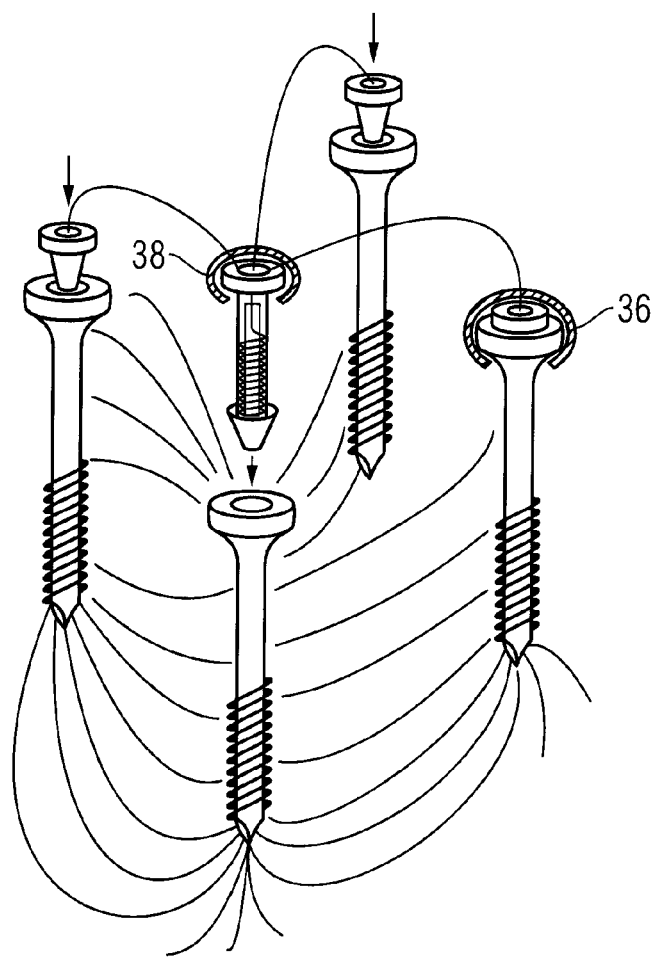
FIG. 3 shows a schematic perspective view an implantation system according to the invention including associated bone screws.
Figure 4:
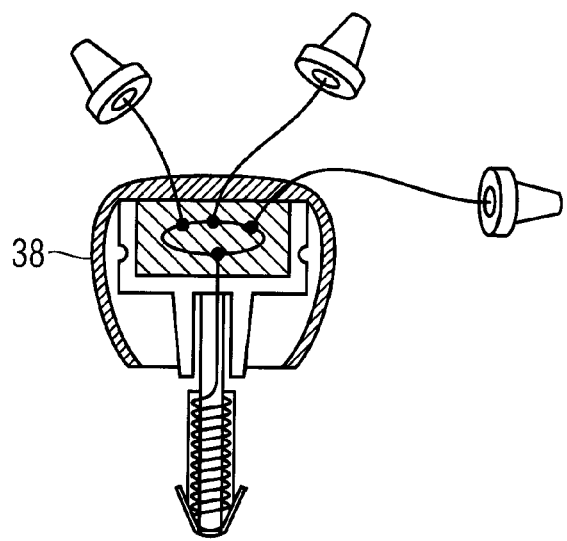
FIG. 4 shows a schematic perspective, partially cut view of a polarization device according to the invention.

FIG. 3 shows a schematic perspective view of an implantation system according to the invention including associated bone screws. FIG. 4 shows a schematic perspective, partially cut view of a polarization device according to the invention. Here it is additionally illustrated that the sections of the polarization device via which the contact devices are coupled to the bone screws may be surrounded by insulating sheaths 36, 38. These insulating sheaths 36, 38 prevent a stimulated bone formation around the insulated areas so that an explantation of the polarization device is facilitated.

Figure 5:
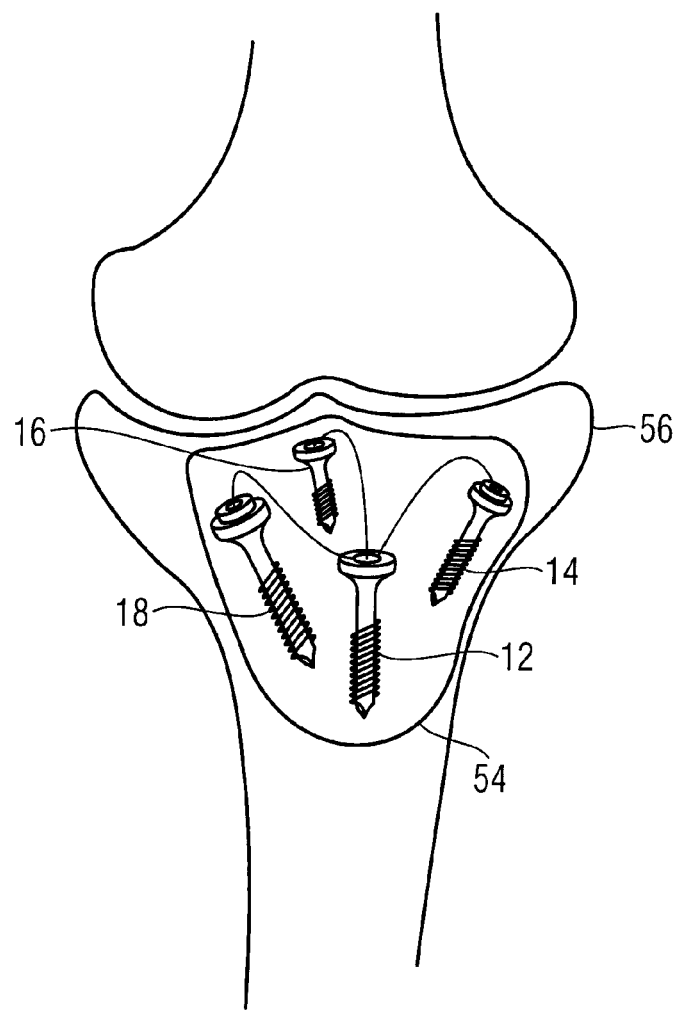
FIG. 5 shows an embodiment of an implantation system according to the invention.

FIG. 5 shows an embodiment of an implantation system according to the invention. It is illustrated how a polarization device according to the invention can be arranged in the area of a tumour 54 in the tibial head 56.

A further, not illustrated embodiment is the screw osteosynthesis of medial femur neck fractures in which several, for example three, screws are deployed which may be functionally connected to each other in the form of the polarization device according to the invention.

Figure 6:
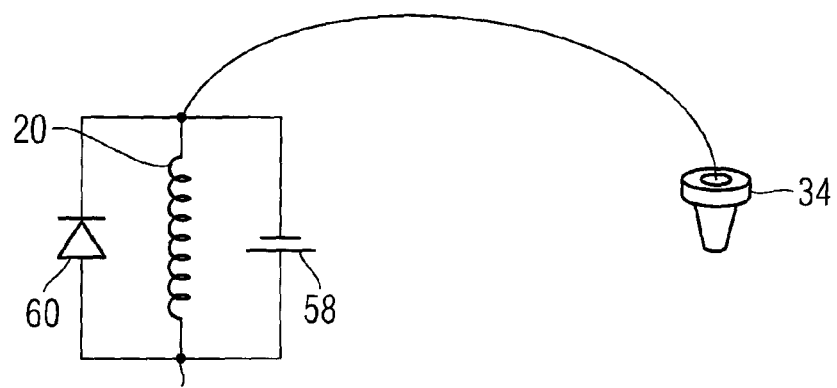
FIG. 6 shows an example of the arrangement of electrical components in a polarization device according to the invention.

FIG. 6 shows an example of the arrangement of electrical components in a polarization device according to the invention. Here it is illustrated that, in parallel to the coil 20, an accumulator 58 may be positioned. To provide the accumulator 58 with a direct voltage to charge it further a rectifier 60, represented by a diode symbol here, is connected in parallel to the assembly of accumulator 58 and coil 20. The accumulator 58 is placed in the spatial vicinity of the coil 20 so that it is placed in the cavity of an implant like the coil 20 if sufficient space is available. Then only a single electric connection has to lead to the contact snap fasteners 34 of which only one is shown by way of example.

Figure 7:
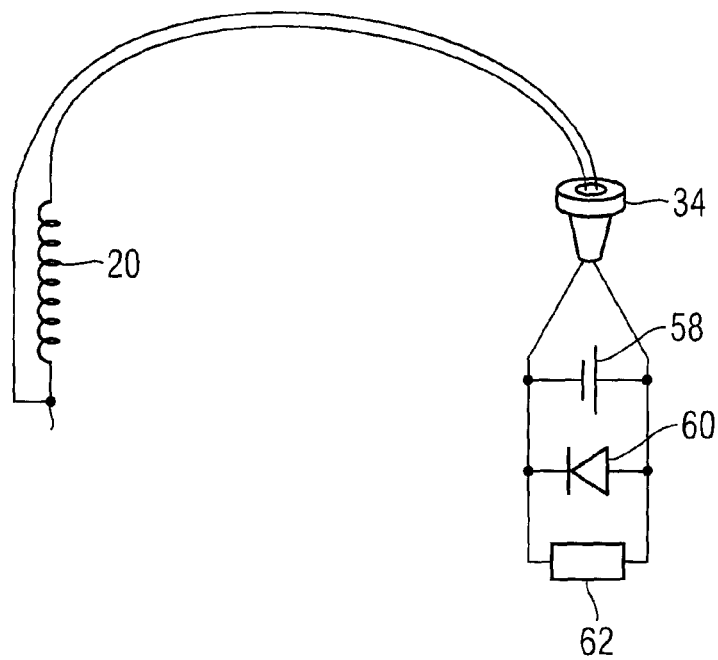
FIG. 7 shows another example of the arrangement of electrical components in a polarization device according to the invention.

FIG. 7 shows another example of the arrangement of electrical components in a polarization device according to the invention. Here the accumulator 58 is also arranged electrically parallel to the coil 20, however, in the vicinity of the contact snap fastener 34. This solution is preferred if the cavity of the implant accommodating the coil 20 is insufficient for the accumulator 58 and the coil 20. Then the accumulator 58 is preferably accommodated in another implant. In this case two electrical lines have to be lead from the area of the implant carrying the coil 20 to the implant carrying the accumulator 58, which can of course be accomplished with a single cable. The parallel connection of an accumulator 58 and the coil 20 enables the accumulator 58 to be charged when the coil 20 is positioned in an external magnetic field. Even in the absence of the external magnetic field an electric voltage can then be maintained between the implants by means of the accumulator 58. However, without further measures the accumulator 58 can only provide a direct voltage without an external magnetic field. However, if the accumulator 58 serves as a voltage source for a function generator 62 as shown in FIG. 7 it can provide an alternating voltage even in the absence of an external magnetic field with the aid of an appropriate contacting of its outputs to the electrically conductive areas of the implants (not shown here).

The features of the invention disclosed in the above description, the drawings as well as the claims may be important for the realisation of the invention individually as well as in any combination.

LIST OF NUMERALS 10 polarization device
12 implant, bone screw
14 implant, bone screw
16 implant, bone screw
18 implant, bone screw
20 coil
22 pole
24 pole
26 contact device
28 contact device
30 line
32 magnetically conductive core
34 contact snap fastener
36 insulating sheath
38 insulating sheath
40 bobbin
42 distributor
44 recess
46 insulating sheath
48 insulating compound
50 housing
52 groove
54 tumour
56 tibial head
58 accumulator
60 rectifier
62 function generator

The invention claimed is:

1. A method for operating an implantable device which polarizes at least two spatially separated, at least partially electrically conductive implants, comprising the acts of:
   implanting the device, the device including
      a coil having a first pole and a second pole;
      a first contact device configured to electrically connect the first pole to a first implant; and
      at least one second contact device configured to electrically connect the second pole to at least one second implant,
   wherein:
      the coil is directly or indirectly arranged on or in the first implant, and
      the at least one second contact device includes a flexible electrical line connectable to the at least one second implant such that the coil is spatially separable from the at least one second implant; and
   operating the device with an alternating voltage such that the first implant has, at least predominantly, a first polarity, while the second implant has, at least predominantly, a second polarity which is inverse to the first polarity,
   wherein the coil is configured to be located in a cavity of the first implant and the first contact device electrically contacts the first implant within the cavity;
   wherein the first implant is a bone screw; and
   wherein the coil is retained by a bobbin through which a mechanical contact to the first implant is established, the mechanical contact comprising a snap-on connection.

2. A device for polarizing at least two spatially separated, at least partially electrically conductive implants, comprising:
   a coil having a first pole and a second pole;
   a first contact device configured to electrically connect the first pole to a first implant; and
   at least one second contact device configured to electrically connect the second pole to at least one second implant,
   wherein
      the coil is directly or indirectly arranged on or in the first implant,
      the at least one second contact device includes a flexible electrical line connectable to the at least one second implant such that the coil is spatially separable from the at least one second implant,
      the coil is configured to be located in a cavity of the first implant and the first contact device electrically contacts the first implant within the cavity, the first implant is a bone screw, and
the coil is retained by a bobbin through which a mechanical contact to the first implant is established, the mechanical contact comprises a snap-on connection.

3. The device according to claim 2, wherein
the coil is part of an electric circuit comprising at least one further electrically effective component.

4. The device according to claim 3, wherein
the at least one further electrically effective component includes an accumulator provided in the electric circuit in parallel to the coil.

5. The device according to claim 4, wherein
the at least one further electrically effective component includes a function generator.

6. The device according to claim 5, wherein
the at least one further electrically effective component includes a circuit component configured to modify an alternating voltage provided by the device so that the first implant has, at least predominantly, a first polarity, while the second implant has, at least predominantly, a second polarity which is inverse to the first polarity.

7. The device according to claim 2, wherein
the bobbin is arranged to accommodate a distributor to which a plurality of second contact devices are connected.

8. The device according to claim 3, wherein
the at least one further electrically effective component is configured to be located in the cavity of the first implant.

9. The device according to claim 3, wherein
the at least one further electrically effective component is configured to be located in a cavity of the second implant.

10. The device according to claim 2, wherein
the at least one second contact device includes a contact snap fastener configured to establish a mechanical and electrical connection to the at least one second implant.

11. The device according to claim 10, wherein
at least one insulating sheath is provided to electrically insulate the contact snap fastener of the at least one second contact device from the surrounding tissue.

12. The device according to claim 2, wherein
the at least one second implant is a bone screw, and
at least one insulating sheath is provided to electrically insulate a proximal area of the bone screw associated with at least one of the first implant and the second implant from surrounding tissue.

13. The device according to claim 2, wherein
at least one insulating sheath is provided to electrically insulate a proximal area of the bobbin from surrounding tissue.

14. The device according to claim 2, wherein
the at least one second implant is a bone screw.

15. The device according to claim 2, wherein
the coil is wound onto a magnetically conductive core.

16. An implantation system comprising:
at least two electrically at least partially conductive implants configured to be implanted in a spatially separated arrangement; and
a device for polarizing the at least two implants according to claim 2.

* * * * *